United States Patent [19]

Rosenberg

[11] 4,301,153

[45] Nov. 17, 1981

[54] HEPARIN PREPARATION

[75] Inventor: Robert D. Rosenberg, Brookline, Mass.

[73] Assignee: Riker Laboratories, Inc., St. Paul, Minn.

[21] Appl. No.: 891,706

[22] Filed: Mar. 30, 1978

Related U.S. Application Data

[62] Division of Ser. No. 779,691, Mar. 21, 1977, abandoned.

[51] Int. Cl.³ .................. A61K 35/14; A61K 31/725; C08B 37/10
[52] U.S. Cl. .................................. 424/183; 424/180; 424/101; 536/21
[58] Field of Search .................. 536/21; 424/183, 101

[56] References Cited

U.S. PATENT DOCUMENTS

| | | | |
|---|---|---|---|
| 3,210,250 | 10/1965 | Bucourt | 536/21 |
| 3,262,854 | 7/1966 | Yasuda | 536/21 |
| 3,932,627 | 1/1976 | Margraf | 536/21 |

OTHER PUBLICATIONS

Lam et al., Biochem. Biophys. Res. Comm., vol. 69, 1976, pp. 570–577.
Lewis et al., Biochem. J., vol. 134, 1973, pp. 455–463.
Nieduszynski et al., Biochem. J., vol. 135, 1973, pp. 729–733.
Highsmith et al., J. Biol. Chem., vol. 249, 1974, pp. 4335–4338.
Rosenberg et al., J. Biol. Chem., vol. 250, 1975, pp. 8883–8888.
Cifonelli et al., Biochemica. et Biophysica. Acta, vol. 320, 1973, pp. 331–340.
Taylor et al., Biochemistry, vol. 13, 1973, pp. 3633–3637.
Rosenberg et al., J. Biol. Chem., vol. 248, 1973, pp. 6490–6505.
"Fluorescamine: A Reagent for Assay of Amino Acids, Peptides, Proteins, and Primary Amines in the Picomole Range", Science, vol. 178, pp. 871–872.
"Anticoagulant Action of Heparin", Nature, vol. 246, 1973, pp. 355–357.
Hook et al. "FEBS Letters", vol. 66, No. 1, 1976, pp. 90–93.

*Primary Examiner*—Johnnie R. Brown
*Assistant Examiner*—Blondel Hazel
*Attorney, Agent, or Firm*—Kenway & Jenney

[57] ABSTRACT

A heparin preparation which exhibits elevated anticoagulant activity and a process for producing the preparation. Conventional heparin exhibiting characteristic anticoagulant activity and molecular heterogeneity is incubated with antithrombin-heparin cofactor extracted from plasma. A portion of the heparin forms a complex with the cofactor. The uncomplexed heparin fraction is then separated from the complexed fraction, and the complexed fraction is broken down to produce cofactor and an active form of heparin.

7 Claims, 3 Drawing Figures

HEPARIN PREPARATION

This is a division of application Ser. No. 779,691 filed Mar. 21, 1977 now abandoned.

BACKGROUND OF THE INVENTION

This invention relates to a method of treating heparin preparations to isolate a heparin fraction having improved anticoagulant activity and to a method of use of the improved preparation.

Heparin is a mucopolysaccharide composed of amino sugar and uronic acid residues which is obtained from beef, porcine, sheep, whale, or other mammalian tissue by extraction with a solution of potassium acetate, alkaline ammonium sulfate and the like. Commercial heparin preparations are now widely available from many U.S. drug companies and are distributed primarily for use as an intravascular anticoagulant. Recently, heparin has been used clinically as a therapeutic agent for preventing intravascular emboli formation which commonly result in pulmonary embolism and stroke.

Heparin preparations are known to be heterogeneous on a molecular level. Thus, they exhibit a considerable degree of polydispersity in molecular size, variations in the ratio of glucuronic acid to iduronic acid, alterations in the amount of ester and N-sulfation, and differing extents of N-acetylation. Changes in any of these parameters have been correlated only to a very limited extent with heparin's anticoagulant potency. Accordingly, it has been widely assumed that its anticoagulant activity is not traceable to a single specific heparin structure, and in any event, no precise relationship between its structure and function has been forthcoming.

The mechanism of the formation of blood clots is known to be the result of a series of enzymatically catalyzed reactions which ultimately result in the production of fibrin, a plasma insoluble protein from which clots are formed. The precursor to fibrin is fibrinogen, a more complex protein which circulates freely in the cardiovascular system and normally comprises between about 3 and 6 percent of the total plasma protein. Fibrinogen is converted to fibrin by the proteolytic enzyme thrombin which is produced as needed from prothrombin. While it has been known for some time that thrombin promotes clotting by its action on fibrinogen, the mechanism of this control has only recently been elucidated and reported.

It has now been reported that antithrombin, another blood protein, reacts with thrombin to form a complex which is incapable of cleaving fibrinogen. Antithrombin has thus been characterized as a thrombin inhibitor. The antithrombin$_{III}$-thrombin reaction normally proceeds at a slow rate. However, it has recently been determined that heparin, if present in the plasma, can rapidly react with antithrombin$_{III}$ to produce a heparin-antithrombin$_{III}$ complex which, probably because of steric modification, can rapidly interact with thrombin to neutralize its ability to cleave fibrinogen. Thus, in blood, heparin rapidly reacts with antithrombin$_{III}$, the complex produced rapidly inhibits thrombin, the neutralized thrombin is incapable of cleaving fibrinogen to fibrin, and the absence of fibrin prevents coagulation.

Coincidentally with the foregoing discoveries, it had been observed that the anticoagulant properties of heparin are operative only in the presence of a plasma component which had been termed "heparin cofactor". It has now become apparent that the thrombin inhibitor identified as antithrombin$_{III}$ and the heparin cofactor are one and the same blood protein. Thus, the anticoagulant activity of heparin may be traced to its ability to dramatically accelerate the rate at which the antithrombin$_{III}$-heparin cofactor (hereinafter referred to as the cofactor) neutralizes thrombin. Furthermore, it has recently been reported that this cofactor, in the presence of heparin, can neutralize the action of serine proteases of the hemostatic mechanism.

SUMMARY OF THE INVENTION

It has now been discovered that only a small fraction of a given heparin preparation can combine with the cofactor (AT) and that this fraction is in the main responsible for heparin's distinctive anticoagulant effect. This discovery has enabled the preparation of heparin characterized by elevated anticoagulant activity, commonly on the order of twice that of presently available preparations.

The heparin of the invention is made from conventional heparin preparations of animal tissue origin which exhibit molecular heterogeity and possess the usual anticoagulant activity. It is produced by incubating a sample of conventional heparin with the cofactor in solution or bound to a solid matrix.

This incubation results in only a portion of the heparin, typically about one-third, becoming complexed with the cofactor. Thus the cofactor is used as an extractant.

If the uncomplexed heparin remaining is then separated from the cofactor bound portion, and then the complex is separated into the cofactor (AT) and heparin, the heparin product comprises a molecular species or a family of molecular species which exhibit significantly increased anticoagulant activity. Specifically, the purified heparin has been observed to have an activity on the order of seven to twenty times that of the heparin species which remain uncomplexed, and two to five times that of the unfractionated heparin from which it was prepared.

This active heparin fraction may be prepared from any commercial heparin preparation, regardless of its method of extraction and source. The cofactor for use as an extractant was made from human plasma but can be made from other mammalian sources such as bovine plasma.

The purified heparin is used in the same manner as presently available heparin, that is, by intravenous injection or subcutaneous administration. However, because of the purified heparin's potentiated anticoagulant activity, less material can be used for a given desired activity level. While, aside from its increased anticoagulant activity, the clinical properties of the purified heparin fraction have not as yet been investigated, it is possible that some of the known undesirable side effects of heparin treatment, such as the onset of thrombocytopenia, osteopenia, etc., might be reduced or eliminated when the purified heparin is used in place of presently available heparin preparations.

Accordingly, objects of the invention include the provision of a method of separating commercially available heparin into active and inactive forms, the provision of an improved heparin for general anticoagulation purpose, and the provision of an improved intravascular anticoagulant. Another object of the invention is to purify commercially available heparin preparations. Still another object is to isolate an active molecular species from heparin samples which are homogeneous at the molecular level.

DESCRIPTION OF THE PREFERRED EMBODIMENT

Figure 1:
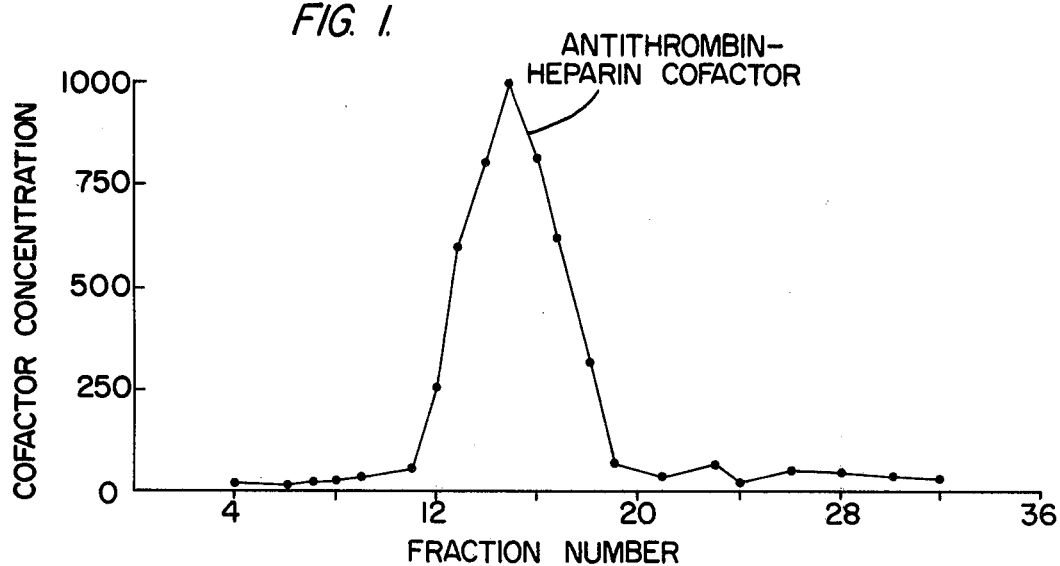
FIG. 1 is a graph illustrating the amount of AT cofactor present in successive fractions produced by subjecting a sample of the AT cofactor isolated from human blood to sucrose density gradient centrifugation.

Physically heterogeneous, heparin samples of the type commonly utilized for anticoagulant therapy of human subjects is the starting material from which the active heparin of the invention is produced. Suitable starting materials are available from commercial drug manufacturers such as Riker Laboratories, Sigma Chemical Company, Organon Corporation, and the Upjohn Company. The process for purifying these preparations involves incubation in an aqueous solution with a sample of AT cofactor, obtained from plasma. Only a portion of the total chemical mass of the commercial heparin sample can react with the AT cofactor to produce a heparin-AT cofactor complex and the remainder appears to be incapable of forming a stable complex. While the amount of heparin which participates in complex formation varies somewhat from one sample to the next, the presence of an active fraction is not limited to a particular heparin starting material.

After reaction, the cofactor bound heparin and unreacted heparin are separated. This results in the active portion of the heparin being eluted with the proteinaceous cofactor. However, the polysaccharide may be readily separated from the protein to produce the heparin fraction of enhanced anticoagulated activity.

It should be noted at this point that a particular method of separating the complexed and uncomplexed heparin fractions from each other, and a particular method of separating the cofactor from the active heparin fraction form no part of the broad inventive concept. Thus, those skilled in the art will readily be able to substitute alternative separation procedures for those disclosed herein. However, the instant procedure does depend on the availability of the AT cofactor, either of human or animal origin. This protein is not commercially available at the present time. However, a useful procedure for its isolation from human plasma is disclosed in detail in an article entitled *The Purification and Mechanism of Action of Human Antithrombin-Heparin Cofactor*, Journal of Biological Chemistry, Vol. 248, pp. 6490–6505, (R. D. Rosenberg, et al., 1973). Briefly, the purification procedure comprises a five-step process wherein the AT cofactor is purified from fresh human plasma by heat defibrination and treatment with barium carbonate, adsorption-elution on aluminum hydroxide, gel filtration on Sephadex G-200, chromatography on DEAE-Sephadex A-50, chromatography on DEAE-cellulose, and preparative isoelectric focusing in sucrose density gradients. This purification method is highly reproducible and, as disclosed below, results in an approximately 11 percent yield.

PURIFICATION OF ANTITHROMBIN COFACTOR (AT)

Step 1

Barium carbonate was added to 1,000 to 1,500 ml of plasma at a concentration of 50 mg per ml. The plasma was gently stirred for 10 min. at 24° and centrifuged for 15 min. at 4° and 2,000×g. The resulting supernatant solution was defibrinated in aliquots of 15 ml by rapidly heating to 54° and holding there for 3 min. The samples were placed on ice for 5 min. and centrifuged at 2,000×g for 15 min. To the combined supernatant solutions, 20% (v/v) aluminum hydroxide was added while stirring. The resulting creamy suspension was stirred continuously for 15 min. at 24° and centrifuged at 2,000×g for 15 min. at 4°. The liquid was discarded and the aluminum hydroxide precipitate was washed with 500 ml of 0.15 M NaCl. To elute AT cofactor activity, 0.36 M ammonium phosphate, pH 8.1, was added to the aluminum hydroxide precipitate in a volume equivalent to 25% of the initial heat-defibrinated supernatant solution, and the suspension was gently agitated for 15 min. at 24°. The cloudy solution was centrifuged at 2,000×g for 15 min. at 4°. The supernatant solution was clarified by centrifugation at 27,000×g for 30 min. at 4° C.

The ammonium phosphate elution of AT cofactor from the aluminum hydroxide was repeated two additional times. However, the third elution utilized only half of the usual volume of ammonium phosphate. All three aluminum hydroxide eluates were combined and concentrated[1] from approximately 540 ml to about 35 ml. A final protein concentration of about 150 absorbance units per ml was achieved. The recovery of AT cofactor, as judged by either immunoassay or activity determination, averaged 55%. The specific activity of these products averaged 10 units per absorbance unit (average specific activity of plasma=2.0 units per absorbance unit).

[1] by ultrafiltration on an Amicon PM30 membrane

The use of fresh plasma is mandatory for optimal yield and maximal specific activity. If frozen plasma is employed, a 25 to 50% reduction in recovery is observed.

For reproducible results, three elutions of the AT cofactor from aluminum hydroxide are of critical importance. Although the first elution may, on occasion, contain 50 to 65% of plasma AT cofactor, it customarily averages 26%. The first elution typically contains 30% of the plasma AT cofactor, while the second and third elution yielded 15% and 5.2% respectively. If these preparations are frozen at either −20° or −90° for 20 hours to 7 days, there is a 60% loss of AT cofactor activity. However, these preparations are stable at 4° for at least 4 weeks.

Step 2

Sephadex G-200 columns (2.5×100 cm or 5.0×100 cm) which are available from Pharmacia Fine Chemicals were equilibrated at 4° with 0.05 M Tris-HCl (tris hydroxy ethyl amine) in 1.0 M NaCl (pH 8.3). The gel matrix was conditioned by an initial filtration with 4 ml of defibrinated plasma per cm² of column cross-section. After the passage of 1 column volume of buffer, the sample eluted from aluminum hydroxide was applied and flow rates of about 3 ml per cm² of column cross-section per hour were maintained with a peristaltic pump. Fractions of 5 to 10 ml were collected and assayed for AT cofactor. Although small amounts of AT cofactor activity were present in the first protein peak, these fractions were discarded. The great bulk of AT cofactor activity emerged together with the albumin present in the starting plasma. When these fractions were pooled, total AT cofactor recovered averaged 65% and specific activity averaged 13 units per absorbance unit.

On occasion, at the completion of a gel filtration, a peak of AT cofactor activity is seen with minimal absorbance at 280 nm. This artifact is usually eliminated by the high speed centrifugation employed in Step 1 and may be due to residual aluminum hydroxide. Step 2 preparations are stable for many weeks at 4° but lose significant activity if frozen at −20° to −90°. Prior to the initiation of Step 3, these preparations were dialyzed for 8 to 12 hours against 10 to 15 liters of 0.1 M Tris-HCl (pH 9.0).

Step 3

[1]DEAE Sephadex A-50 was packed into a column (5.0×30 cm), 2,000 absorbance units of dialyzed Step 2 material were applied, and a linear salt gradient was employed for fractionation with the reservoir containing 1200 ml of 0.25 M NaCl in 0.1 M Tris-HCl (pH 9.0). Chromatography was conducted at 4° C. with flow rates maintained at 67 ml/min. with a peristaltic pump. Fractions of 13 ml were collected. The AT cofactor was eluted over a range of 0.02 M NaCl and with the peak of activity centered at an added ionic strength of 0.11 M NaCl. With different lots of DEAE-Sephandex A-50, the added NaCl concentration required to elute maximal amounts of the AT cofactor varied from 0.11 M NaCl to 0.14 M NaCl. However, the range of ionic strength over which the AT cofactor was eluted, the purity, and the yield of the Step 3 product were independent of the DEAE-Sephadex A-50 lot number. This step has an average yield of 73% and an average specific activity of 134 units per absorbance unit. If stored at 4°, Step 3 fractions were stable for 4 to 6 weeks. Prior to Step 4, Step 3 preparations were dialyzed for 8 to 12 hours against 4 liters of 0.1 M Tris-HCl (pH 8.3).
[1]diethyl amino ethyl Step 4

DEAE-cellulose (DEAE-32) was packed into a column (2.5×40 cm). One hundred forty absorbance units of the dialyzed Step 3 fraction were applied. This purification step employed a linear salt gradient with the mixing chamber containing 950 ml of 0.1 M Tris-HCl buffer (pH 8.3), and the reservoir containing 950 ml of 0.1 M NaCl in 0.1 M Tris-HCl (pH 8.3). During the chromatography at 4°, flow rates were maintained at 40 ml per hour with a peristaltic pump and fractions of 103 ml were collected. The AT cofactor emerges over a narrow ionic strength range of 0.008 M NaCl and the peak of activity is centered at an added ionic strength of 0.068 M NaCl. These chromatographic parameters have been remarkably constant for several lots of DEAE-cellulose. The recovery of AT cofactor activity was 66% for Step 4 and the specific activity averaged 494 units per absorbance unit. Since only fractions with specific activity of 360 units per absorbance unit or greater were pooled, true AT cofactor recovery is underestimated by approximately 15%. Rechromatography of Step 4 preparations on DEAE-cellulose yielded only a modest 15% increase in specific activity and therefore was not utilized.

The pooled Step 4 fractions were concentrated from 100 ml to about 4 ml by ultrafiltration.

Step 5

Isoelectric focusing in an LKB S102 column was performed with pH 4 to 6 carrier ampholytes (1.7%) (LKB-Produckter, AB, Sweden). The AT cofactor has an isoelectric point of 5.11 and distributes predominantly over 0.15 pH unit. The recovery of AT cofactor activity averages 65% and its specific activity averages 900 units per absorbance unit. Measurements of AT cofactor activity from pH 5.0 to 5.15 yield superimposable gaussian profiles. When fractions 93 to 102 were examined by polyacrylamide disc gel electrophoresis, sodium dodecyl sulfate gel electrophoresis, or Immunoelectrophoresis, a single sharp band was seen. Occasionally, trace amounts of a more rapidly moving impurity were found. Fractions above #102 had increasing quantities of impurity which may amount to 5% of the major band. Fractions below 93 had a second component which had a mobility slightly lower than AT cofactor on disc gel electrophoresis. In this region of the pH gradient, AT cofactor and the impurity were preceived as a closely split doublet. This final step of the fractionation yields identical results when the protein content of the sample is increased from 17 absorbance units to 35 to 50 absorbance units.

Ampholytes have been removed from AT cofactor preparations either by extensive dialysis or by filtration through conditioned Sephandex G-50 columns (1.25×60 cm).

At this point it should be noted that the foregoing procedure for producing the AT cofactor is a laboratory procedure which has been described in the literature and which can be employed in practicing the present invention. However, the following procedure for producing the AT cofactor can be used to greater advantage in a commercial scale-up of the present invention.

The following procedure involves a prior art method for preparation of heparin, a prior art technique for binding of heparin to sepharose, and a method for utilizing the heparin-sepharose matrix for the isolation of large quantities of AT cofactor.

PREPARATION OF HEPARIN

Four grams of crude heparin (Wilson stage 14) was placed into 500 ml of 1.2 M NaCl which had been preheated to 40° C. At the same time 12.7 g of CPC (cetyl pyridinium chloride) was placed into 900 ml of 12 NaCl preheated to 90° C. The two fluids were mixed together and incubated over night at 40° C. The scum which formed at the top of the fluid was subsequently harvested and dissolved in 100 ml of 3 M NaCl (total volume 120 ml). The material was diluted with water such that the ionic strength became 1.2 M NaCl (∼180 ml). After formation of a white precipitate, the mixture ws incubated for 2-2.5 hours at 40°. The scum was again harvested and centrifuged at 11,000×g for 25 min. at 22° C. The fluid was discarded and the scum and precipitate were thoroughly dissolved in 100 ml of 3 M NaCl which had been preheated to 40° C.

Three hundred milliliters of ethanol was added (3:1) and the material was again centrifuged at 11,000×g for 25 min. at 22° C. The supernatant was discarded and the precipitate dissolved in 100 ml of 3 M NaCl (40°) and recentrifuged at 11,000×g for 25 min. (22°).

After discarding the supernatants once more, the precipitate was dissolved in 50 ml of H$_2$O. Subsequently, 150 ml of EtOH was added and the precipitate scraped off the walls. Finally the material was centrifuged at 11,200×g for 25 minutes at 22° and the material was utilized for attachment to sepharose.

PROCEDURE FOR SEPHAROSE ACTIVATION

Sepharose 4B, or some other insoluble matrix, is washed in a sintered glass funnel with 1 liter of H$_2$O. Seventy five milliliters of the packed gel are mixed with an equal volume of H$_2$O. To this 150 ml of suspension is added on iced solution of 2.25 g CnBr (cyanogen bromide) dissolved in 75 ml H$_2$O. Once the CnBr is mixed, the pH is continuously monitored and kept at pH 11 or above for 5 min. Then the matrix is washed with 3.5 liters of iced H$_2$O. Finally the gel is washed with 1 liter of iced 0.1 M NaHCO$_3$. Then 200 mg of heparin is dissolved in 50 ml of 0.1 M NaHCO$_3$, pH 8.5 and added to the gel. The mixture is brought to 150 ml by the addition of 0.1 M NaHCO$_3$, pH 8.5 and incubated for 16 hours while stirring. Subsequently, 7.5 ml of either ethanolamine or of 1 M glycine pH 8.5 are added and stirring is continued for an additional 4 hours. The gel mixture was washed with 1 liter of iced H$_2$O, 1.5 liters of iced 0.5 M NaCl and 3 liters of 0.15 M NaCl in 0.01 M Tris pH 7.5. This heparin-sephrose matrix was stored at 4° with 0.1% solution of sodium azide prior to use for the purification of cofactor.

PREPARATION OF COFACTOR BY THE HEPARIN-SEPHAROSE METHOD

Three hundred milliliters of "settled" heparin-sepharose gel matrix were washed with 2 liters of 0.145 M NaCl and 1% sodium citrate in 0.01 M Tris pH 8.3 (HCl). After most of the fluid was aspirated, the heparin-sepharose was mixed with 2 liters of plasma and incubated for 30 min. at 24° C. while stirring. The cofactor is adsorbed to the heparin sepharose during this incubation. Thus the remainder of plasma is removed by filtration through a sintered glass funnel and discarded. The cofactor heparin-sepharose matrix is washed by batching with 150 ml of the 0.145 M NaCl and 1% sodium citrate in 0.01 Tris pH 8.3 buffer. The buffer is drawn off. A little fresh buffer is added and the material is packed into a 35×4.8 cm column. The column is washed with approximately 170 ml of 0.4 M NaCl and 1% sodium citrate in 0.01 M Tris pH 8.3 buffer flowing at 7-10 ml/hr at 4°. The AT cofactor was then eluted with a buffer of 2 M NaCl and 1% sodium citrate in 0.01 M Tris pH 8.3. Flowing at 5-7 ml/hr, the AT cofactor peak occurred at approximately 266 ml of effluent. All fractions containing protein were pooled and dialyzed against a buffer of 0.02 M NaCl and 1% sodium citrate in 0.01 M Tris pH 8.3 for 4.5 hrs. This material was concentrated by ultrafiltration on an [1]Amicon PM 30 membrane and processed on DEAE Sephadex (diethyl amino ethyl).

[1]Manufactured by Amicon Corporation, Lexington, Mass.

The DEAE cellulose utilized (DE 52 Whatman) for this purpose is washed with 0.5 M NaOH-0.5 M NaCl and then with 0.5 M HCl-0.5 M NaCl and again with 0.5 M NaOH-0.5 M NACl and then with 0.5 M HCl-0.5 M NaCl followed by 1.2 liters of 0.14 M NaCl in 0.1 M Tris pH 8.3. This material is packed into a 100×2.5 cm column and allowed to settle for 0.5 hr. prior to use.

The cofactor is pumped onto this column at a flow rate of 6 ml/hr and is adsorbed to the DEAE matrix. The protein is then eluted by developing a gradient of ionic strength between 0.04 M NaCl in 0.01 M Tris and 0.1 M NaCl in 0.01 M Tris pH 8.3. The AT cofactor peaks at 175 ml and an added ionic strength of 0.07 M NaCl. Fractions which contain AT cofactor activity and are homogeneous by gel electrophoresis are pooled.

PRODUCTION OF HEPARIN WITH ENHANCED ACTIVITY

In accordance with the invention, the cofactor produced as described above, preferably in a two-fold molar excess, is admixed with a commercial heparin preparation in aqueous solution. Incubation at 37° C. for 1 to 2 minutes results in the formation of a heparin cofactor complex, and it is the heparin which undergoes this reaction which comprises the material that must be cleaved to produce cofactor and a heparin with enhanced anticoagulant activity.

A suitable method of separating the complex from unbound heparin involves sucrose density gradient centrifugation. After dialysis, the samples of the reaction mixture are overlayed on sucrose density gradients and centrifuged. This technique produces fractions which vary in their concentration of complex and uncomplexed heparin. Typically, in a run involving about 34 fractions, fractions 1-15 contain complexed heparin and the remaining fractions contain the inactive species.

The complex comprises a proteinaceous moiety and the uncomplexed heparin is a polysaccharide. Accordingly, there are several known methods of separating these molecular species. Thus, the heparin fractions bound to the cofactor are pooled, dialyzed, and subjected to chromatography with DEAE cellulose. If the chromographic matrix is first washed with 0.25 LiCl, protein is eluted. The muco polysacchride content may be harvested with 2 M LiCl. The heparin content of a particular fraction may be determined colorimetrically by assay of uronic acid via the carbazole method (see, Anal. Biochem. 4:330-334 T. Bitter, et al.) or by a modification of the Azure A method (see, J. Physiol. 109: 41-48, L. B. Jaques, et al.). The amount of protein in a particular sample may be determined by fluorometric assay using, for example, fluorescamine, which is known to react with primary amines to produce an easily detectable fluorophor (see, Science, 1972, 178: 871-872, S. Udenfriend, et al.).

The foregoing procedure results in recovery of approximately 70% of the active heparin which was bound to the complex. It will be obvious to those skilled in the art that other methods of separating the active heparin fraction may be employed without departing from the scope of the instant invention. For example, high salt concentrations, low or high pHs can be employed to break the heparin-AT cofactor complex and harvest the heparin. Furthermore, it is clear that in any commercial production of the potentiated heparin, it will be highly desirable to reuse the AT cofactor for successive extractions. In this regard, it is possible, for example, to immobilize the cofactor on a suitable support, contact heparin samples with the immobilized cofactor to effect complex formation, and thereafter elute the purified heparin without removing the bound AT cofactor.

To prepare an affinity matrix which can recognize and bind "activating" regions within glycosaminoglycans, AT cofactor is linked to a bland resin while allowing the heparin binding site free access to solvent.

The sepharose matrix is known to be contaminated with sulfated polysaccharides. These components might interact with bound AT cofactor and prevent complex formation with appropriate regions on oligosaccharides or glycosaminoglycans. Therefore, the matrix might be desulfated in order to convert sepharose into a bland resin.

It is advisable but not essential to protect the heparin binding site during linkage of AT cofactor to sepharose. This is accomplished by binding the polysaccharides to the AT cofactor prior to experimental manipulation. The interaction product is quite stable within a defined range of pH and ionic strength.

To develop the optimal way of binding AT cofactor heparin complexes to sepharose, a variety of amino acid residues can be employed in the linkage of this macromolecule to the resin. For example, these might include $\epsilon$-amino lysyl groups (cyanogen bromide method), imidazole, and phenolic residues (DVS method). Furthermore, spacers can be employed so that the protein-heparin complex is at some physical distance from the resin surface (CnBr or DVS method).

After preparation of the AT cofactor-sepharose matrix, it can be washed with a high ionic strength buffer to elute protecting heparin from the AT cofactor. Ionic strengths of $>0.3$ will disrupt this interaction. It is possible that heparin used to protect the AT cofactor site may be covalently bound to sepharose by prior experimental manipulations aimed at linking the protein to the resin. If this occurs, the sepharose can be treated with purified mucopolysaccharides to eliminate this difficulty.

Once prepared, this affinity matrix is used to selectively bind highly active heparin fractions. These components can be eluted with increasing gradients of ionic strength at a specific pH. The ionic strength at which active heparin fraction eluted is ionic strength $>0.6$.

The invention will be further understood by the following non-limiting examples.

PREPARATION OF ACTIVE HEPARIN VIA AFFINITY MATRIXES

A commercially available matrix such as Sepharose 4B or Sepharose 4B-CL (desulfated) was activated with cyanogen bromide as described earlier except that glycine was not utilized to block unoccupied activated sites or with divinylsulfone as described below. A ten fold molar excess of unfractionated commercial heparin was added to purified AT cofactor so as to form the heparin-AT cofactor complex and thereby protect the AT cofactor site from binding to the matrix. Then the protected AT cofactor was admixed with the activated matrix at a ratio of 100 μg of AT cofactor to 1 Mg of AT cofactor per ml of sepharose. The reaction was allowed to proceed for 16–24 hrs. at 0°–40° C. with constant stirring. After completion of this procedure, each volume of matrix was washed with 10 volumes of 2 M NaCl and then 5 volumes of 0.1 M sodium phosphate (pH 7.0). This affinity matrix was placed into appropriate sized columns, 25–200 units of heparin equilibrated in 0.1 M sodium phosphate buffer, pH 7.0 was filtered through 2 ml of AT cofactor-sepharose and the column was washed with two column volumes of 0.05 M NaCl in 0.1 M sodium phosphate buffer, pH 7.5. Finally, the bound heparin was eluted with 2.0 M NaCl in 0.1 M sodium phosphate, pH 7.5. The heparin fractions were dialyzed against several changes of 0.15 M NaCl in 0.01 M Tris HCl, pH 7.5. The specific activity of the eluted fractions corresponded to approximately 290–350 units/mg (initial specific activity = 155 units/mg). Therefore, the heparin fractions had been purified to approximately 2–2.5 fold over the starting material.

PRIOR ART LONG ARM DVS SEPHAROSE BINDING PROCEDURE

Step One

1. Filter and wash sepharose CL-4B with H$_2$O
2. Weight out X grams (approximately X ml of settled resin)
3. Add resin to 4.5 X ml of 1 M sodium carbonate pH 11.0 (adjusted with 4 N NaOH as necessary) while stirring
4. Add 0.02 X ml divinylsulfone (DVS, Aldrich) and react 20 minutes with stirring under hood
5. Filter and wash quickly with 5 X ml 1 M sodium carbonate pH 11.
6. Add 0.06 X grams p-nitrobenzyl alcohol in X ml of 50% aqueous dimethylformamide (DMF) and react at least 8 hours with stirring at room temperature.

Step Two

1. Filter and wash with 5 X ml each 50% DMF, methanol, and then 0.5 M NaHCO$_3$, pH 8.5.
2. Suspend in 2.5 X ml of 0.5 M NaHCO$_3$, pH 8.5 and reduce at 40° C. for 1 hour with stirring by adding dry sodium dithyonite (mw 174.11) to a final concentration of 0.2 m moles/ml (34.3 mg/ml gel suspension, 0.122 X grams).
3. Filter and wash with 5 X ml each 0.5 M NaHCO$_3$, pH 8.5, distilled H$_2$O, and 0.5 N Hcl.
4. Suspend in X ml *ice cold* 0.5 N Hcl and stir 7 mins. on ice.
5. Add X ml 0.1 M NaNO$_2$ (fw 69) and stir 7 mins. on ice.
6. Filter and wash with 2.5 X ml *ice cold* 0.5 N and 2.5 X ml *ice cold distilled* H$_2$O.
7. Add quickly to protein solution (protein in X ml of *ice cold* pH 8.5 0.1 M NaHCO$_3$) [partition as desired].
8. Adjust the pH to 8.0 (histidine) or pH to 10 (tyrosine) with *ice cold* 4 N NaOH. React overnight at 0° to 4° C. with stirring.

Step Three

1. Filter and wash with 10 X ml of 2 M NaCl
2. Wash with 5 X ml of 0.5 M NaCl
3. Resuspend in appropriate buffer (X ml gives a convenient consistency).

PREPARATION OF HEPARIN WITH ENHANCED ACTIVITY VIA SUCROSE DENSITY GRADIENT CENTRIFUGATION

Figure 2:
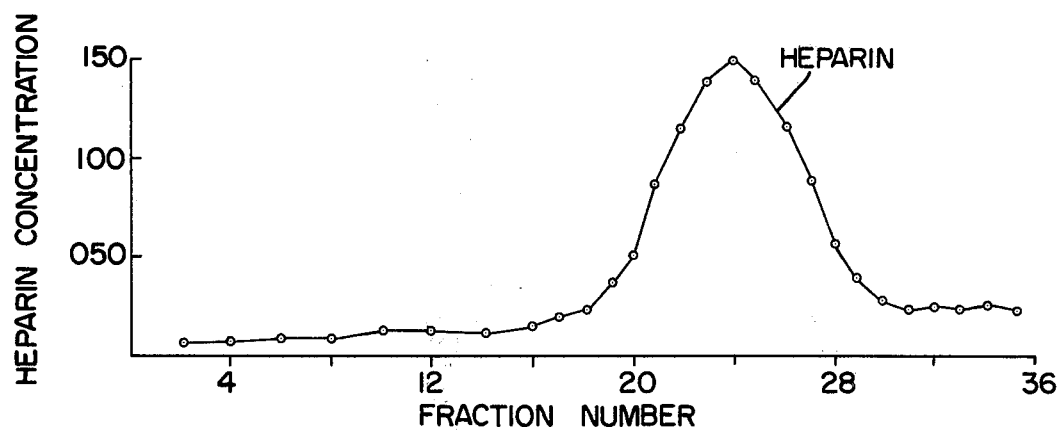
FIG. 2 is a graph similar to FIG. 1 illustrating the amount of heparin present in successive fractions produced by subjecting a commercially available heparin preparation to sucrose density gradient centrifugation; and, FIG. 3 is a graph similar to those of FIGS. 1 and 2 illustrating both AT cofactor and heparin concentration in successive fractions of a mixed sample produced by sucrose density gradient centrifugation.

A 10 μg sample of unfractionated heparin (33.3 μg/ml) which had been extensively dialyzed against 0.15 M NaCl in 0.01 M sodium phosphate (pH 7.5), was overlayed on 4.7 ml of 10–15% (w/v) sucrose density gradients in which the solvent was 0.15 M NaCl in 0.01 M sodium phosphate (pH 7.5). After centrifugation at 224,000 xg for 20 hours at 4° C., the bottom of each tube was punctured and fractions were collected for analysis. As shown in FIG. 2, a single narrow peak of heparin was apparent which indicated high heparin concentration at fraction 18–30.

A sample containing 100 μg of dialyzed AT cofactor obtained in the manner set forth above was examined by sucrose density gradient centrifugation in a manner identical to that used for the heparin preparation except that the final concentration of the cofactor was 333 μg/ml. Centrifugation followed by collection of fractions and assay indicated that a concentration of protein was present in fractions 10-18 (See FIG. 1).

Figure 3:
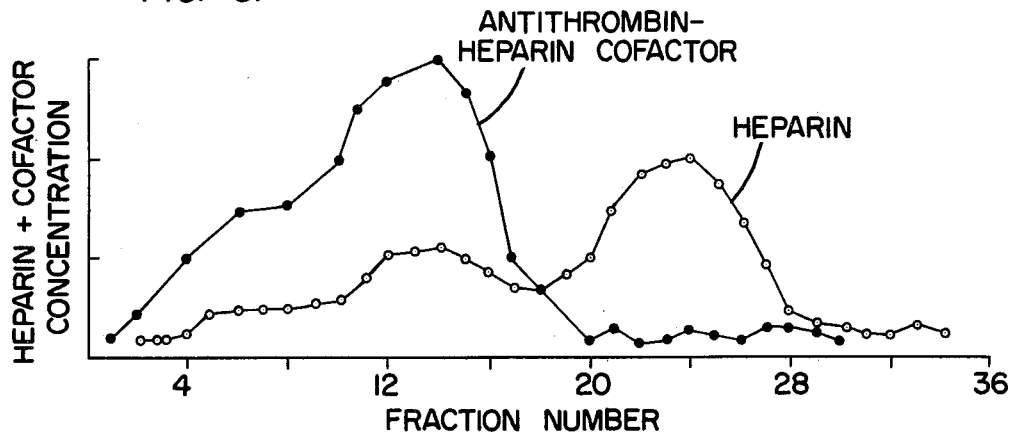

By comparing the graphs of FIGS. 1 and 2, it can be seen that single, narrow, nonoverlapping peaks of protein and heparin were produced. However, when both components were mixed together and incubated briefly at the same final concentrations and under the same solvent conditions as employed in the separate examinations, centrifugation and collection of samples produced two major alterations in the component distribution pattern. These are illustrated in FIG. 3. The first change noted was in the profile of the AT cofactor which revealed a significant degree of polydispersity with large amounts of protein present at relatively high sedimentation velocities (fractions 2-11). A shift in the sedimentation velocity of the AT cofactor peak to a slightly higher value was also apparent. Second, it was noted that heparin was no longer present as a discrete peak, but rather was distributed throughout the density gradient.

Thus, it can be seen from FIG. 3 that approximately ⅓ of the heparin is located under the AT cofactor peak. This suggested that it had been drawn into this region due to an interaction with the AT cofactor. Approximately ⅔ of the heparin preparation was present in its original position in the density gradient, and therefore appeared to be incapable of forming a stable complex with the AT cofactor. This latter observation was surprising in that a three-fold molar excess of the AT cofactor was present in the original reaction.

From the foregoing, it was assumed that heparin bound to the cofactor might represent an active species, while the uncomplexed heparin could signify a chemically similar but inactive form.

To validate this hypothesis, the anticoagulant activity of each of the heparin species was quantitated. Accordingly, fraction were collected from either the areas of density gradient free of protein (fractions 21-28) or from the regions in which heparin was gound to AT cofactor (fractions 3-15). Fractions were pooled from 6 to 12 individual density gradients and were extensively dialyzed and assayed for anticoagulant activity as well as haparin content. The results of these measurements are set forth in Table I below.

TABLE I

SPECIFIC ANTICOAGULANT ACTIVITY*
OF HEPARIN SAMPLES

| Experiment | Unfractionated Heparin | Heparin Bound To Antithrombin-Heparin Cofactor | Uncomplexed Heparin |
|---|---|---|---|
| 1 | 155 | 388 | 19 |
| 2 | 155 | 365 | 52 |
| 3 | 155 | 348 | 43 |

*anticoagulant activity per mg of heparin.

Separation of protein from the samples were effected by absorbing samples pooled from fractions 3-15 (FIG. 3) containing 0.6 mg. of cofactor and 25 μg of complexed heparin of a DEAE-cellulose column (0.85 by 1.8 cm). The chromatographic matrix was washed with 5 ml of 0.25 M LiCl to differentially elute protein, and the mucopolysaccharide was harvested with 2 M LiCl. Approximately 70% of the formerly complexed heparin could be recovered by this procedure, and only about 1% of the initial cofactor present in the mix remained. Additional experiments demonstrated that the specific activity of the haparin was not altered by the above technique.

As can be seen from the results set forth in Table I, the average specific activity obtained for the heparin fractions which were unable to bind with the cofactor was 38 units/mg whereas heparin that had been complexed averaged 367 units/mg. This, of course, is considerably higher than the specific activity of the unfractionated heparin (155 units/mg).

In a separate experiment, it was determined that fractionation of this active heparin form was dependent on the presence of the AT cofactor. Attempts to duplicate the isolation using bovine serum albumin, a plasma protein similar in size to the cofactor, were unsuccessful. Indeed, as judged by sucrose density gradient centrifugation, heparin does not interact with this plasma component.

The heparin utilized as a starting material in this experiment is essentially indistinguishable from other commercially available heparin preparations. Furthermore, analysis of heparin obtained from a mouse mass cell tumor, although characterized by an anticoagulant activity somewhat lower than the porcine preparations used in this example, have been observed to produce a similar pattern of fractionation with 30% of the heparin's chemical mass containing 95% of its biological activity.

The foregoing indicates that heparin preparations consist of at least two distinct forms which differ greatly in their ability to bind to the cofactor and activate its inhibiting function. Since it is now well established that the mechanism of heparin's anticoagulant activity involves the formation of a cofactor - heparin complex, it is apparent that the heparin fraction having the ability to bind to the cofactor comprises one or more molecular species which exhibit significantly enhanced anticoagulant activity.

As can be seen from the data set forth above, one third of the total chemical mass of the unfractionated heparin is responsible for approximately 85% of the total anticoagulant activity of the material. The other two thirds of the chemical mass of the heparin which do not bind tightly to AT cofactor is responsible for only about 15% of the anticoagulant activity. This relatively low anticoagulant potency may be an inherent property of this molecular species or could be due to residual contamination with the more active form.

The heparin of the invention is used in a manner identical to that of conventional heparin preparation to inhibit blood coagulation. However, for a given desired level of anticoagulant activity, less heparin may be employed. Of course, the quantities used and frequency of administration will vary. As is known, if heparin is used as an intravascular coagulant, it must be introduced parenterally.

Both examples of enhanced activity heparin fractionation have employed techniques for the determination of heparin concentration as well as anticoagulant activity. These procedures are described below.

PRIOR ART ASSAYS OF HEPARIN CONCENTRATION

The mucopolysaccharde concentration of a heparin sample was determined colorimetrically by assay of uronic acid via the carbazole method and by a modification of the Azure A method. When this latter method was utilized, 50 μl of a sample (0–5 μg) was added to 1 ml of Azure A (0.01 mg/ml in distilled water). The resultant mixture was agitated and absorbance at 500 nm was measured. Sucrose concentrations from 10% to 50% (w/v) and AT cofactor levels from 20 μg/ml to 290 μg/ml had, essentially, no effect upon this assay. The heparin concentration of all fractionated samples was determined by comparison with the initial starting material. The standard titration curve of this unfractionated sample exhibited a linear rise in absorbance at 500 nm from 0 to 0.200 as the amount of heparin was increased from 0 to 5 μg. Correlations have been established between these assay procedures and the dry weights of heparin preparations.

ASSAY OF ANTICOAGULANT ACTIVITY

The anticoagulant activity of the unfractionated heparin preparations were assumed to be equivalent to the U.S.P. unitage cited on its label. The potency of all fractionated heparin samples was determined by comparison with this starting material. To construct a standard titration curve, 50 μl of AT cofactor (50 μg/ml) were added to 20 μl aliquots of various dilution of the reference sample. The resultant mixtures were incubated for 1–2 min. at 37°. Then 280 μl of 0.135 M NaCl in 0.05 M Tris-Imidazole (ph 8.3) was admixed with the latter solutions prior to the addition of 50 μl of human thrombin (~60 N.I.H. units/ml or ~25 μg/ml). After 30 sec. of incubation at 37°, 300 μl of substrate were introduced and the reaction mixtures were incubated for an additional 60 sec. at 37°. The substrate consisted of Benzoyl-Phen-Val-Arg-p-Nitroanilide. HCl (AB Bofors, Nobel Division, Molndal, Sweden), and polybrene dissolved in H₂O with each component at a final concentration of 0.33 mg/ml. Finally, 300 ml of galcial acetic acid was added to quench the action of thrombin upon the tripeptide and the extend of amidolysis was quantitated by measuring the absorbance of samples at 405 nm. All determinations were preformed in triplicate. The titration curve of the heparin reference standard exhibited a linear decline in absorbance from ~0.8 to ~0.2 when heparin concentrations ranged from 0 to 1 unit/ml. To measure the anticoagulant activity of a fractionated heparin sample, it was diluted to approximately 0.5 units/ml. and assayed with the above technique by comparison with the reference standard. This technique has been compared to the standard U.S.P. assay of heparin anticoagulant activity and has been found to result in specific activities (units of anticoagulant activity/mg of heparin) which are 20 to 30% lower than those found by the U.S.P. assay. Furthermore, non-specific effects which are found in the U.S.P. assay are not present in our assay procedure.

PRIOR ART FLUOROMETRIC ASSAY OF PROTEIN CONCENTRATION

The concentration of AT cofactor which was present in the sucrose density gradient example was quantitated by the following technique.

Fifty μl of a sample (0 to 100 μg of AT cofactor) was added to 250 μl of 0.2 M sodium borate buffer (pH 9.0). Then 100 μl of a solution containing fluorescamine dye (0.1 mg/ml in acetone) was injected while vortexing the solution and the final volume of the resultant mixture was brought to 2 ml with the buffer described above. The fluorescence of this solution was read at 475 nm after excitation at 390 nm. A standard titration curve exhibited a linear increase in relative fluorescence from 0 to 1000 as the level AT heparin cofactor was varied from 0 to 100 μg. Concentrations of heparin below 140 μg/ml have essentially no effect on this assay of protein concentration.

At this point, it should be noted that the foregoing discussion has been directed to purifying heparin with commercially available heparin as the starting material. However, the invention is not intended to be limited to this specific scheme. In connection with this point, the present process has great applicability as part of a technique for obtaining elevated activity heparin immediately after extraction from animal tissue. It should be noted that although mammalian tissues are the present preferred source of heparin, other animal sources such as clams can be utilized as the starting material.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. A process for producing heparin characterized by elevated anticoagulant activity, said process comprising the steps of:
   A. providing a heparin preparation of animal tissue origin which exhibits molecular heterogeneity and anticoagulant activity;
   B. providing AT cofactor extracted from mammalian plasma;
   C. incubating the heparin preparation with the AT cofactor to complex a portion of the heparin with the cofactor;
   D. separating a complex of heparin and cofactor from the remainder of the heparin preparation; and,
   E. separating the cofactor from the complex to produce heparin having improved anticoagulant activity.

2. The process as set forth in claim 1 wherein the heparin preparation provided in step A is extracted from tissue selected from the group consisting of beef, porcine, sheep, and whale tissue.

3. The process as set forth in claim 1 wherein the heparin produced in step E has at least twice the anticoagulant activity of the heparin preparation provided in step A.

4. The process as set forth in claim 1 wherein the AT heparin cofactor provided in step B is extracted from human plasma.

5. A potentiated heparin preparation prepared from heparin of animal tissue origin which has been complexed with AT cofactor, separated from heparin uncomplexed with AT cofactor, and separated from the heparin AT cofactor complex to yield a heparin preparation having greater anticoagulant activity than heparin from the animal tissue origin.

6. A process for inhibiting coagulation of blood, said process comprising the steps of:
   A. providing a heparin preparation of animal tissue origin which exhibits molecular heterogeneity and anticoagulant activity;
   B. providing AT cofactor extracted from mammalian plasma;

C. incubating the heparin preparation with the AT cofactor to complex a portion of the heparin with the cofactor;
D. separating a complex of heparin and cofactor from the remainder of the heparin preparation;
E. separating the cofactor from the complex to produce heparin having improved anticoagulant activity; and,
F. mixing the potentiated heparin with blood.

7. The process as set forth in claim 6 wherein the potentiated heparin is mixed with blood by injecting the potentiated heparin subcutaneously.

* * * * *